Aug. 15, 1972 W. H. JESSEL, JR., ETAL Plant Pat. 3,254
CHRYSANTHEMUM PLANT
Filed Jan. 8, 1971
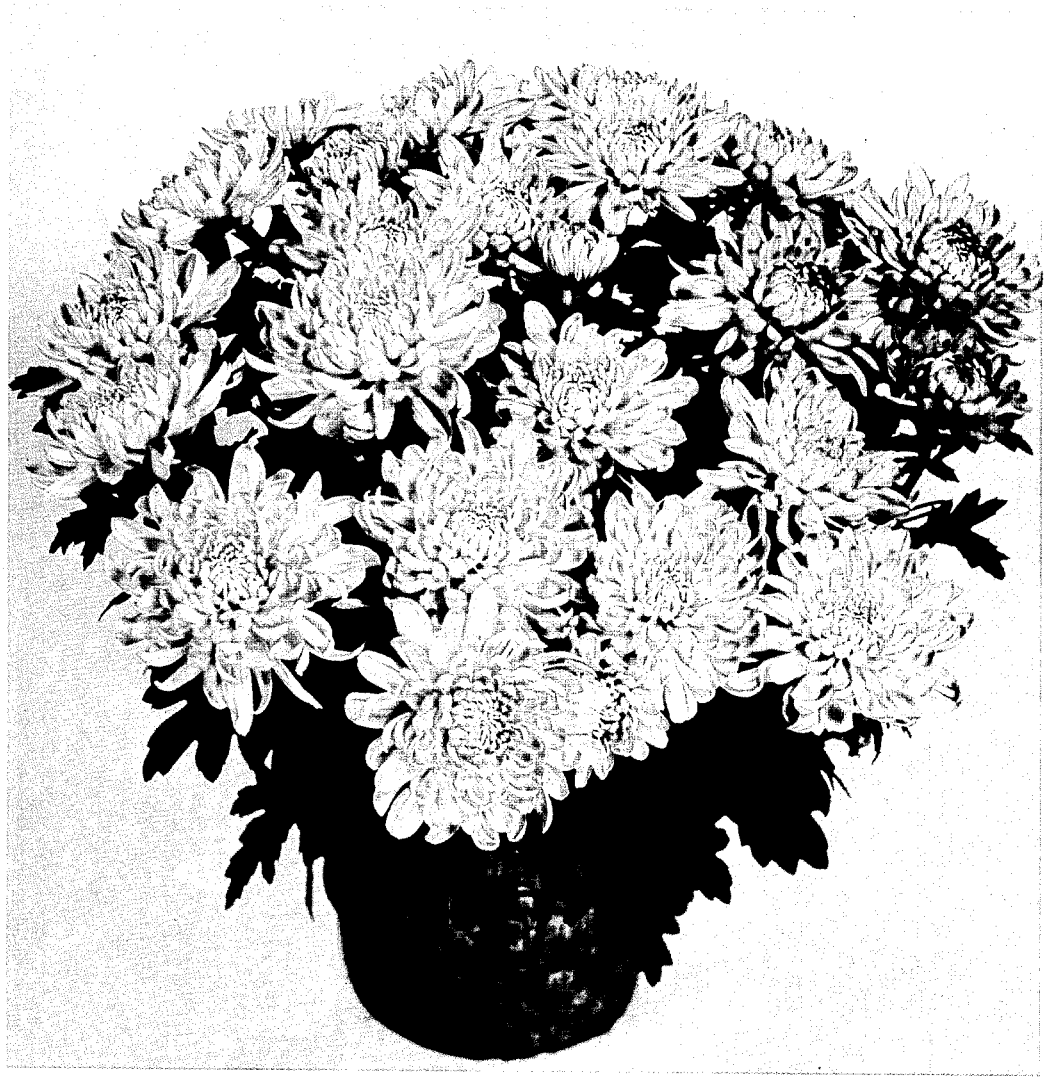
INVENTORS
WALTER H. JESSEL, JR.,
WILLIAM E. DUFFETT
BY
Oberlin, Maky, Donnelly & Renner
ATTORNEYS

United States Patent Office

Plant Pat. 3,254
Patented Aug. 15, 1972

3,254

CHRYSANTHEMUM PLANT

Walter H. Jessel, Jr., Doylestown, and William E. Duffett, Akron, Ohio, assignors to Yoder Brothers, Inc., Barberton, Ohio

Filed Jan. 8, 1971, Ser. No. 105,137
Int. Cl. A01h *5/00*
U.S. Cl. Plt.—81 1 Claim

The present invention comprises a new and distinct cultivar of chrysanthemum plant which is a sport of the unpatented but commercially well-known cultivar known in the United States as Conquest.

The new cultivar is similar in many respects to the parent cultivar Conquest, having the same characteristics of:

(1) Plant habit.
(2) Flower size.
(3) Flower form.
(4) Nine week response.

The new cultivar when grown in the vicinity of Barberton, Ohio, has a response period of approximately nine weeks, and the following detailed description is based on observations made of the new cultivar in a greenhouse in Barberton, Ohio. The response time, blooming period, color, and total vigor may vary significantly with varying environmental conditions such as temperature, day length, and light intensity. Suggested flowering in the northern and western United States is from September through May; in Coastal California, January through December; and in Florida, from mid-October through mid-April.

The accompanying drawing shows the unique characteristics of the new cultivar, the color being as nearly true as possible with color illustrations of this type. In the following description, color references are to the Munsell Color Book, 1963 edition, comparisons have been made in certain instances with the cultivar Conquest. Where only the value or description of the new cultivar appears, such value or description applies also to the comparison cultivar.

BOTANICAL CLASSIFICATION: *Chrysanthemum morifolium*

| | Deep conquest | Conquest |
|---|---|---|
| Bloom: | | |
| Size | 4". | |
| Fully expanded | 4¾". | |
| Borne | Terminal on disbudded plants. | |
| Stems | Strong. | |
| Form | Semi-incurve. | |
| Permanence | 10–14 days. | |
| Color: | | |
| Center of flower | Greenish yellow, 10Y8/8 | Greenish yellow, 10Y8/8. |
| Base of petals | Lavender, 2.5RP6/8; Light lavender, 2.5RP8/4 | Light lavender, 2.5RP8/4; Pale lavender, 2.5RP9/2. |
| Inside of petals | do | Light lavender, 2.5RP8/4; Pale lavender, 2.5RP9/2. |
| Reverse of petals | Light lavender, 2.5RP8/4; Pale lavender, 2.5RP9/2 | Pale lavender, 2.5RP9/2; Very pale lavender, 10P9/1. |
| Tonality from a distance | Lavender | Light lavender. |
| Discoloration | Light lavender | Very pale lavender. |
| Petals: | | |
| Texture | Smooth. | |
| Appearance and form | Open at base, broaden quickly, *very* shallow keel tapering to a blunt, slightly notched point. | |
| Arrangement | Composite, whorled on a single receptacle. | |
| Persistence | Resist shatter. | |
| Fragrance | Typical chrysanthemum. | |
| Reproductive organs: | | |
| Stamen, anthers | 0–5. | |
| Pollen | None to very scant. | |
| Arrangement | Clustered in center of flower, if present. | |
| Styles | Present both ray and disc florets. | |
| Length | Short. | |
| Ovaries | At the base of petal attached to receptacle. | |
| Plant: | | |
| Form | Herbaceous. | |
| Growth | Semi-upright. | |
| Height | 10–11". | |
| Spread | Moderate. | |
| Foliage: | | |
| Top side | Dark green 10GY3/4. | |
| Size | 4" long, 2¼" wide. | |
| Quantity | Numerous. | |
| Shape | Spatulate lobed. | |
| Texture | Smooth. | |
| Ribs and veins | Prominent. | |
| Edge | Indented. | |
| Serration | Fine. | |
| Underside | Light green 7.5GY5/4. | |
| Stipules | Small. | |

The new cultivar is distinguished from Conquest by the following characteristics:

(1) A deeper lavender flower color.

(2) A greater resistance to fading under high light, high temperature conditions, thereby extending the recommended flowering period, without air-cooling, an additional two months in the northern United States.

The new cultivar was selected from a flowering block of the parent cultivar in Barberton, Ohio, and when asexually reproduced by cutting at Barberton, Ohio, the new cultivar has been found to retain its distinctive characteristics through successive propagations.

We claim:

1. A new and distinct cultivar of chrysanthemum characterized particularly as to uniqueness when compared with the parent cultivar Conquest by its darker lavender pink flower color which provides a deeper shade, and by its greater resistance to high heat, high light conditions, thereby extending the recommended flowering period in the northern United States by an additional two months.

No references cited.

ROBERT E. BAGWILL, Primary Examiner